(12) United States Patent
Lin et al.

(10) Patent No.: US 11,278,582 B2
(45) Date of Patent: Mar. 22, 2022

(54) COMPOSITIONS CONTAINING PLANT EXTRACTS AND APPLICATIONS THEREOF

(71) Applicant: TCI CO., LTD., Taipei (TW)

(72) Inventors: Yung-Hsiang Lin, Taipei (TW); I-Hui Chen, Taipei (TW); Kai-Wen Kan, Taipei (TW); Fu Chen Liu, Taipei (TW); Ciao-Ting Chen, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

(21) Appl. No.: 16/499,666

(22) PCT Filed: Apr. 3, 2018

(86) PCT No.: PCT/CN2018/081707
§ 371 (c)(1),
(2) Date: Sep. 30, 2019

(87) PCT Pub. No.: WO2018/184521
PCT Pub. Date: Oct. 11, 2018

(65) Prior Publication Data
US 2020/0038468 A1  Feb. 6, 2020

Related U.S. Application Data

(60) Provisional application No. 62/480,860, filed on Apr. 3, 2017, provisional application No. 62/503,185, filed on May 8, 2017.

(51) Int. Cl.
| | | |
|---|---|---|
| *A61K 36/00* | (2006.01) |
| *A61K 36/185* | (2006.01) |
| *A23L 33/105* | (2016.01) |
| *A61K 9/00* | (2006.01) |
| *A61K 9/08* | (2006.01) |
| *A61K 9/48* | (2006.01) |
| *A61P 3/04* | (2006.01) |
| *A61K 31/01* | (2006.01) |
| *A61K 31/015* | (2006.01) |
| *A61K 36/21* | (2006.01) |
| *A61K 36/258* | (2006.01) |
| *A61K 36/31* | (2006.01) |
| *A61K 36/45* | (2006.01) |
| *A61K 36/48* | (2006.01) |
| *A61K 36/53* | (2006.01) |
| *A61K 36/67* | (2006.01) |
| *A61K 36/73* | (2006.01) |
| *A61K 36/74* | (2006.01) |
| *A61K 36/752* | (2006.01) |
| *A61K 36/815* | (2006.01) |
| *A61K 36/82* | (2006.01) |
| *A61K 36/87* | (2006.01) |
| *A61K 36/886* | (2006.01) |
| *A61K 36/8962* | (2006.01) |
| *A61K 36/9066* | (2006.01) |
| *A61K 8/9789* | (2017.01) |
| *A61P 17/16* | (2006.01) |
| *A61Q 19/00* | (2006.01) |
| *A23F 3/16* | (2006.01) |
| *A61K 8/97* | (2017.01) |
| *A61Q 17/04* | (2006.01) |
| *A61P 19/04* | (2006.01) |
| *A61Q 19/08* | (2006.01) |

(52) U.S. Cl.
CPC ............ *A61K 36/185* (2013.01); *A23F 3/163* (2013.01); *A23L 33/105* (2016.08); *A61K 8/97* (2013.01); *A61K 8/9789* (2017.08); *A61K 9/0056* (2013.01); *A61K 9/0095* (2013.01); *A61K 9/08* (2013.01); *A61K 9/48* (2013.01); *A61K 31/01* (2013.01); *A61K 31/015* (2013.01); *A61K 36/21* (2013.01); *A61K 36/258* (2013.01); *A61K 36/31* (2013.01); *A61K 36/45* (2013.01); *A61K 36/48* (2013.01); *A61K 36/53* (2013.01); *A61K 36/67* (2013.01); *A61K 36/73* (2013.01); *A61K 36/74* (2013.01); *A61K 36/752* (2013.01); *A61K 36/815* (2013.01); *A61K 36/82* (2013.01); *A61K 36/87* (2013.01); *A61K 36/886* (2013.01); *A61K 36/8962* (2013.01); *A61K 36/9066* (2013.01); *A61P 3/04* (2018.01); *A61P 17/16* (2018.01); *A61P 19/04* (2018.01); *A61Q 17/04* (2013.01); *A61Q 19/007* (2013.01); *A61Q 19/08* (2013.01); *A23V 2002/00* (2013.01)

(58) Field of Classification Search
CPC ...................................................... A61K 36/00
USPC ......................................................... 424/725
See application file for complete search history.

(56) References Cited

U.S. PATENT DOCUMENTS 8,129,337 B2 * 3/2012 Wolfram ............... A61K 38/018
514/5.7

FOREIGN PATENT DOCUMENTS

| CN | 101623038 | * | 1/2010 |
| CN | 101909610 | A | 12/2010 |
| CN | 103549061 | * | 2/2014 |
| CN | 105851308 | * | 8/2016 |
| CN | 105875963 | | 8/2016 |
| CN | 105875963 | A | 8/2016 |

(Continued)

OTHER PUBLICATIONS

The Government of India, The Biological Diversity Act, 2002.
(Continued)

*Primary Examiner* — Michael V Meller
(74) *Attorney, Agent, or Firm* — Chieh-Mei Wang

(57) ABSTRACT

Provided is a composition for reducing the fat content of fat-producing cells and applications thereof. The composition includes plant extracts such as a blueberry extract and a black tea extract.

3 Claims, 2 Drawing Sheets

(56) References Cited

FOREIGN PATENT DOCUMENTS

| CN | 106070466 | * | 11/2016 |
| JP | 2011-132150 | * | 7/2011 |
| TW | 201540294 A | | 11/2015 |

OTHER PUBLICATIONS

Examination report dated May 7, 2021, listed in correspondent China patent application No. 201880021260.3 (publication No. CN 110461348 A).

Search report dated Jan. 8, 2019, listed in correspondent Taiwan patent application No. 107111688 (publication No. TW 201836626).

Research progress on efficacy of Bluberries., Wang et al., vol. 35 No. 14, Jul. 31, 2015, Chinese Journal of Gerontology, pp. 4082-4084.

Study on the weight loss effect and mechanism of tea on obese rats., Wang Tieh, vol. 1, Jan. 15, 2013, China Master's Theses Full-text Database, featured Agricultural Science and Technology, pp. 47-315.

Progress on functionality of blueberry and extracting technology for its active ingredient, Li et al. Vol. 31 No. 6, Nov. 25, 2015, pp. 251-254.

Studies have found that drinking red wine in moderation may help obesity, Huang Min, Xinhua Daily Telegraph, Apr. 16, 2012, Ver. 7, p. 1, Full Text.

Study on the corpulent-reducing function of tea, Gong et al., Journal of tea Science, 2007, 27(3), pp. 179-184, Full Text.

Wang, Qian, "Research on Efficacy of Blueberries", Chinese Journal of Gerontology, Jul. 31, 2015, p. 4082-4084.

Wang, Die, Studies on Anti-Obesity Effects of Tea Extracts on High Fat Diets Induced Obese Rats and Their Potential Mechanisms, Agriculture, China Mater's Theses Full-Text Database, No. 1, Jan. 15, 2013, D047-315.

* cited by examiner

US 11,278,582 B2

COMPOSITIONS CONTAINING PLANT EXTRACTS AND APPLICATIONS THEREOF

CROSS-REFERENCE TO RELATED APPLICATION

This application is a National Stage Entry of PCT application PCT/CN2018/081707, filed on Apr. 3, 2018, which claims priority of U.S. Provisional Application No. 62/480,860, filed on Apr. 3, 2017, and U.S. Provisional Application No. 62/503,185, filed on May 8, 2017, the content of which is incorporated herein in its entirety by reference.

BACKGROUND OF THE INVENTION

1. Field of the Invention

The present invention relates to a composition containing plant extracts and applications thereof, and in particular, relates to a composition for reducing the fat content of fat-producing cells and applications thereof.

2. The Prior Art

Most modern people have concerns of obesity due to high-fat and high-sugar diets and insufficient exercise, and therefore have a higher probability of suffering from metabolic diseases such as diabetes, hyperlipidemia, hypertension, cardiovascular diseases, and fatty liver diseases, which are serious threat to individual's health. Scientific studies also show that obesity is an important causing factor of cancers. In addition, obese people are more prone to psychological problems and social disorders. Therefore, a lot of medical research in recent years has focused on seeking approaches to obesity prevention, whereby promoting physical and mental health.

Methods of inhibiting obesity include diet control, exercise, lifestyle changes, medication, and surgery. Surgery is required only by severe obese patients, whereas the general public usually loses weight by diet control and exercise. This is because the modern busy-working people have difficulty changing their lifestyles, and they are reluctant to take non-essential medication because of a belief in natural therapies. However, diet control requires dietary balance and calorie intake strictly; and inappropriate exercise regimes may cause physical damage. In addition, these two methods have limited effect on weight loss because they are not directed against fat cells, especially adipose tissue in the viscera.

In view of this, it is of necessity to develop a composition that is convenient for the public to use and effective in reducing the fat content of fat cells, so as to prevent obesity and reduce the risk of suffering from the various metabolic diseases and cancers described above.

SUMMARY OF THE INVENTION

Accordingly, in one aspect, the present invention provides a composition including a plant extract, wherein the composition includes a combination selected from the group consisting of a blueberry extract and a black tea extract, a blueberry extract and a green tea extract, a red wine extract and a black tea extract, a red wine extract and a green tea extract, a red wine extract and a Pu-erh tea extract, a red wine extract and a Four Seasons Spring tea extract, a red wine extract and a citrus extract, a red wine extract and a spinach extract, a red wine extract and a green coffee bean extract, a citrus extract and a broccoli sprout extract, a citrus extract and a red clover extract, a citrus extract and an aloe extract, a citrus extract and a rosemary extract, a citrus extract and a garlic extract, a citrus extract and a pepper extract, a citrus extract and a turmeric extract, a citrus extract and a wolfberry extract, a citrus extract and a ginseng extract, a citrus extract and apple polyphenols, a citrus extract and β-carotene, a citrus extract and lycopene, a spinach extract and a red clover extract, a spinach extract and a rosemary extract, a spinach extract and a garlic extract, a spinach extract and a turmeric extract, a spinach extract and a wolfberry extract, a spinach extract and a ginseng extract, a spinach extract and apple polyphenols, and a spinach extract and β-carotene.

In one embodiment of the present invention, the composition including the blueberry extract includes at least 0.0625 mg/ml of the blueberry extract and at least 0.0625 mg/ml of any one of the black tea extract and the green tea extract.

In one embodiment of the present invention, the composition including the red wine extract includes at least 0.0625 mg/ml of the red wine extract and at least 0.0625 mg/ml of any one of the black tea extract, the green tea extract, the Pu-erh tea extract, the Four Seasons Spring tea extract, the citrus extract, the spinach extract, and the green coffee bean extract.

In one embodiment of the present invention, the composition including the citrus extract includes one of the following combinations: at least 0.015625 mg/ml of the citrus extract and at least 0.015625 mg/ml of any one of the apple polyphenols and the lycopene; at least 0.0625 mg/ml of the citrus extract and at least 0.0625 mg/ml of the rosemary extract; at least 0.125 mg/ml of the citrus extract and at least 0.125 mg/ml of any one of the broccoli sprout extract, the turmeric extract, and the ginseng extract; at least 0.5 mg/ml of the citrus extract and at least 0.5 mg/ml of any one of the red clover extract, the pepper extract, and the β-carotene; or at least 1 mg/ml of the citrus extract and at least 1 mg/ml of any one of the aloe extract, the garlic extract, and the wolfberry extract.

In one embodiment of the present invention, the composition including the spinach extract includes one of the following combinations: at least 0.015625 mg/ml of the spinach extract and at least 0.015625 mg/ml of the apple polyphenols; at least 0.0625 mg/ml of the spinach extract and at least 0.0625 mg/ml of the rosemary extract; at least 0.125 mg/ml of the spinach extract and at least 0.125 mg/ml of any one of the turmeric extract and the ginseng extract; at least 0.5 mg/ml of the spinach extract and at least 0.5 mg/ml of any one of the red flower extract and β-carotene; or at least 1 mg/ml of the spinach extract and at least 1 mg/ml of any one of the garlic extract and the wolfberry extract.

In another aspect, the present invention provides a pharmaceutical composition, including any one of the above-mentioned composition and a pharmaceutically acceptable carrier.

In one embodiment of the present invention, the pharmaceutical composition may be in the form of a solution, a powder, a capsule, or a tablet.

In yet another aspect, the present invention provides a use of any one of the abovementioned composition for reducing the fat content of fat-producing cells, or a use of any one of the abovementioned composition in the manufacture of a pharmaceutical composition for reducing the fat content of fat-producing cells.

Due to the mix of particular plant extracts or the mix of a particular plant extract and a particular plant-derived compound, the composition of the invention greatly reduces the fat content of fat-producing cells, thereby having the potential to reduce body fat and to prevent obesity associated diseases. In other words, administration to a subject an effective amount of the composition of the invention can reduce fat levels in that subject. Therefore, the composition of the invention may be used in the manufacture of a pharmaceutical composition for reducing the fat content of fat-producing cells.

BRIEF DESCRIPTION OF THE DRAWINGS

The accompanying drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1:
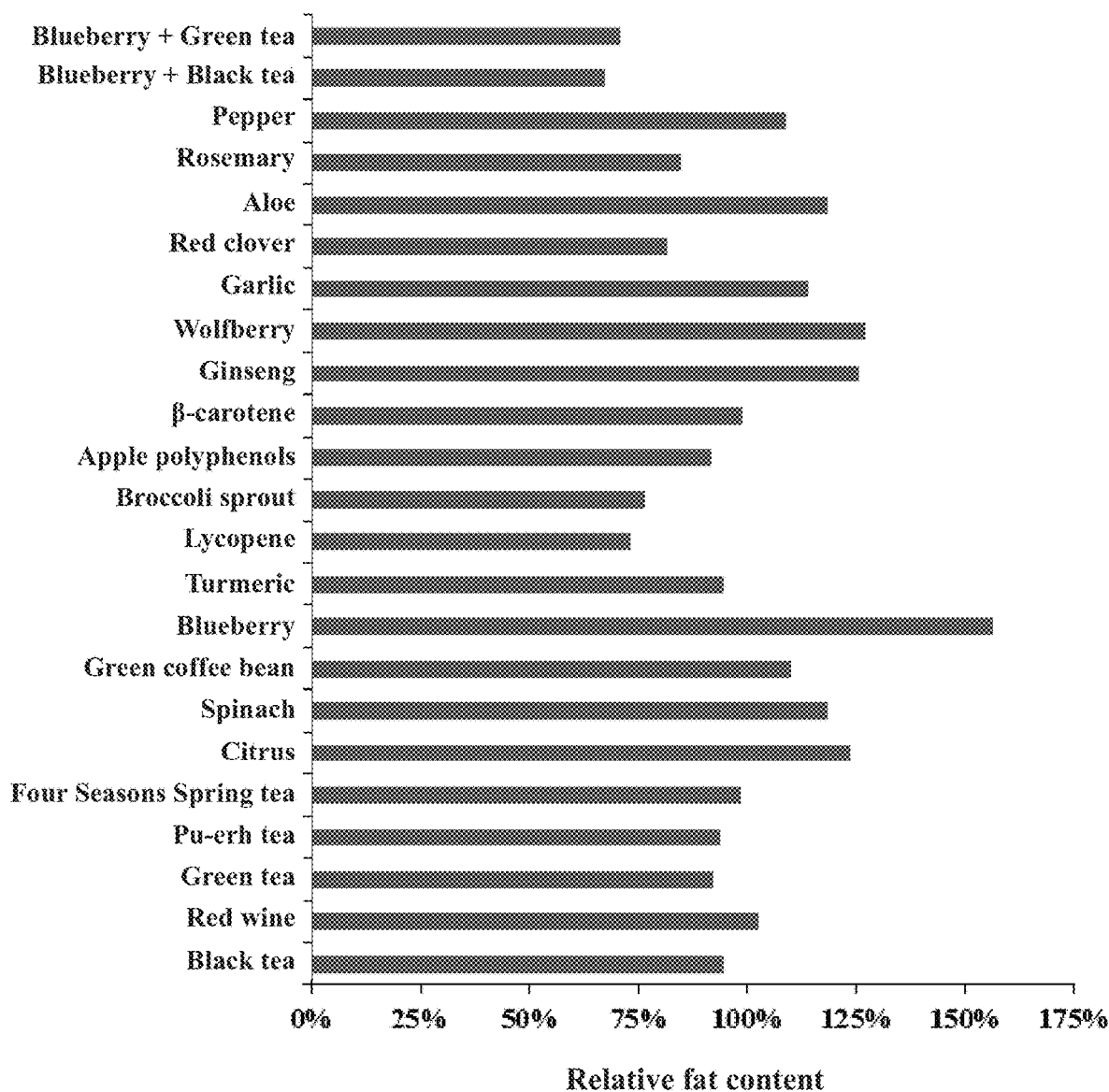
FIG. 1 shows the effect of the various compositions according to one embodiment of the invention on the relative fat content of adipocytes.

The embodiments of the present invention are further described below, in reference to the accompanying drawings. Examples are set forth below to illustrate the features and applications of the present invention, and are not intended to limit the scope of the present invention. Those of ordinary skill in the art will appreciate that various changes and modifications may be made without departing from the spirit or scope of the present disclosure, which is defined in the appended claims.

Definition

Numerical quantities provided herein are approximated values. All experimental values may vary within 20 percent, preferably within 10 percent, and most preferably within 5 percent of the given values.

As used herein, "fat-producing cell" refers to any mammalian cell that functions by synthesizing and storing neutral fats. The fat-producing cells include mature adipocytes that are differentiated and neonatal adipocytes.

As used herein, "pharmaceutically acceptable carrier" refers to one or more solid or liquid vehicles which are not toxic to mammals and which do not affect the biological activity of an active ingredient in a composition.

The present invention provides a composition for reducing the fat content of fat-producing cells. The composition contains either a plurality of plant extracts or a plant extract and plant-derived compounds. The composition is prepared by mixing the extract of black tea, green tea, Pu-erh tea, Four Seasons Spring tea, red wine, green coffee beans, blueberry, citrus, spinach, broccoli (*Brassica oleracea* var. *italica*) sprouts, red clover, aloe, rosemary, garlic, pepper, turmeric, wolfberry, or *ginseng*, or prepared by mixing the aforementioned plant extract with apple polyphenols, beta carotene, or lycopene. The following examples disclose that said composition can greatly reduce the fat content of fat-producing cells.

Materials and Methods

Materials

Dulbecco's modified Eagle's medium (DMEM), fetal bovine serum (FBS), penicillin/streptomycin, and phosphate buffered saline (PBS) were purchased from Gibco. Oil red O was purchased from Sigma. Formaldehyde and isopropanol were purchased from Echo Chemical. Apple polyphenols were purchased from Giwan Ltd. Beta carotene (β-carotene) was purchased from Goodwin International Trading Co., Ltd. Lycopene was purchased from Hunan Naturalin Bio-Resources Co., Ltd.

Oil Red O Staining and Quantitative Analysis

The neutral fat content of cells was determined by oil red O staining. Prior to staining, the cells were washed twice with PBS and then fixed with 10% formaldehyde at room temperature for 30 minutes. The fixed cells were washed twice with PBS and rinsed with 60% isopropanol for 1 minute. Thereafter, the cells were stained with an oil red O staining solution (1.8 mg/ml oil red O dissolved in 60% isopropanol aqueous solution) for 1 hour, and then treated with 60% isopropanol for 5 seconds to remove excess dye. Lastly, 100% isopropanol was added to the cells and incubated with shaking for 10 minutes to dissolve the intracellular dye, and the absorbance of the cell suspension at 510 nm was measured using an ELISA (enzyme-linked immunosorbent assay) reader (BioTek). The statistical significance of differences between data was determined by Student's t-test using the Excel software.

Example 1 Preparations of Plant Extracts 1-1 Black Tea Extract

This example exemplifies the method of preparing a black tea extract. Black tea leaves (the fermented leaves of *Camellia sinensis*) are first washed, dried, and crushed coarsely with a pulverizer. Next, the coarsely crushed black tea leaves are extracted with water as the solvent, wherein the solvent and the coarsely crushed black tea leaves are mixed uniformly at a liquid-solid ratio of 5-20:1-5, and the extraction temperature is between 50° C. and 100° C., preferably between 75° C. and 95° C. The extraction time is about 0.5 to 3 hours. After cooled to room temperatures, the black tea extract obtained from the extraction step is filtered through a 400 mesh filter to remove solid residues. The filtered black tea extract may further be concentrated under reduced pressure at 45° C. to 70° C. to obtain a concentrated product.

1-2 Green Tea Extract

This example exemplifies the method of preparing a green tea extract. Green tea leaves (the unfermented leaves of *Camellia sinensis*) are first washed, dried, and crushed coarsely with a pulverizer. Next, the coarsely crushed green tea leaves are extracted with water as the solvent, wherein the solvent and the coarsely crushed green tea leaves are mixed uniformly at a liquid-solid ratio of 5-20:1-5, and the extraction temperature is between 50° C. and 100° C., preferably between 75° C. and 95° C. The extraction time is about 0.5 to 3 hours. After cooled to room temperatures, the green tea extract obtained from the extraction step is filtered through a 400 mesh filter to remove solid residues. The filtered green tea extract may further be concentrated under reduced pressure at 45° C. to 70° C. to obtain a concentrated product.

1-3 Pu-Erh Tea Extract

The Pu-erh tea extract is obtained by extracting Pu-erh tea leaves (post-fermented leaves of *Camellia sinensis*). The extract may be purchased from Nanjing Zelang Biotechnology Co., Ltd.

1-4 Four Seasons Spring Tea Extract

This example exemplifies the method of preparing a Four Seasons Spring tea extract. Four Seasons Spring tea leaves (the leaves of the Four Seasons Spring tea plant) are first washed, dried, and crushed coarsely with a pulverizer. Next, the coarsely crushed Four Seasons Spring tea leaves are extracted with water as the solvent, wherein the solvent and the coarsely crushed Four Seasons Spring tea leaves are mixed uniformly at a liquid-solid ratio of 5-20:1-5, and the extraction temperature is between 50° C. and 100° C., preferably between 75° C. and 95° C. The extraction time is about 0.5 to 3 hours. After cooled to room temperatures, the Four Seasons Spring tea extract obtained from the extraction step is filtered through a 400 mesh filter to remove solid residues. The filtered Four Seasons Spring tea extract may further be concentrated under reduced pressure at 45° C. to 70° C. to obtain a concentrated product.

1-5 Red Wine Extract

The red wine extract is obtained by extracting red wines. The extract may be purchased from Shanghai Boyoutang Biotechnology Co., Ltd.

1-6 Green Coffee Bean Extract

The green coffee bean extract is obtained by extracting unroasted seeds of *Coffea* spp. plants. The extract may be purchased from ARJUNA NATURAL EXTRACTS Ltd (India).

1-7 Blueberry Extract

The blueberry extract is obtained by extracting the fruit of North American blueberry (*Vaccinium cyanococcus*). The extract may be purchased from Biomed Herbal Research Co., Ltd.

1-8 Citrus Extract

The citrus extract is obtained by extracting the fruit of mandarin orange (*Citrus reticulata*). The extract may be purchased from Roterm Trading Co., Ltd.

1-9 Spinach Extract

The spinach extract is obtained by extracting spinach (*Spinacia oleracea*). The extract may be purchased from Hong Siang Farm Products Factory.

1-10 Broccoli Sprout Extract

The broccoli sprout extract is obtained by extracting the sprout of broccoli (*Brassica oleracea* vat: *italica*). The extract may be purchased from Chori Co., Ltd (Japan).

1-11 Red Clover Extract

The red clover extract is obtained by extracting red clover (*Trifolium* pretense). The extract may be purchased from Material World Industrial Co. Ltd.

1-12 Aloe Extract

The aloe extract is obtained by extracting Aloe vera. The extract may be purchased from Ambe Phytoextracts Pvt. Ltd (India).

1-13 Rosemary Extract

The rosemary extract is obtained by extracting rosemary (*Rosmarinus officinalis*). The extract may be purchased from Jiajing Baica Co., Ltd.

1-14 Garlic Extract

The garlic extract is obtained by extracting the bulb of garlic (*Allium sativum*). The extract may be purchased from Changsha Huir Biological Tech Co., Ltd.

1-15 Pepper Extract

The pepper extract is obtained by extracting the fruit of pepper (*Piper nigrum*). The extract may be purchased from Material World Industrial Co. Ltd.

1-16 Turmeric Extract

The turmeric extract is obtained by extracting the rhizome of turmeric (*Curcuma longa*). The extract may be purchased from ARJUNA NATURAL EXTRACTS Ltd. (India).

1-17 Wolfberry Extract

The wolfberry extract is obtained by extracting the fruit of wolfberry (*Lycium chinense*). The extract may be purchased from Hunan Huakang Biotech Inc.

1-18 Ginseng Extract

The ginseng extract is obtained by extracting the root of *Panax ginseng*. The extract may be purchased from Hunan Huacheng Bio, Inc.

Example 2

Reduction of the Fat Content in Fat-Producing Cells by Compositions Containing Plant Extracts To examine the effect of the composition of the invention on the fat storage of fat-producing cells, oil red O staining was employed to monitor changes in the fat content of the adipocytes differentiated from OP9 mouse stromal cell line (ATCC CRL-2749) and treated with the indicated plant extracts or combinations thereof. Briefly, OP9 cells were seeded at $8 \times 10^4$ cells/well in 24-well culture plates, where each well contained 500 μl of pre-adipocyte expansion medium (90% DMEM, 20% FBS, and 1% penicillin/streptomycin), and cultured at 37° C. for 7 days. The medium was refreshed every 3 days during cell culture with adipocyte differentiation medium (90% DMEM medium, 20% FBS, and 1% penicillin/streptomycin). After 7 days, complete differentiation into adipocytes were confirmed by examining oil droplets formed in the cells using a microscope (ZEISS; at 400× magnification). Thereafter, each of the plant extracts or each of the compositions containing plant extracts, listed in TABLE 1, was added to the cells, which were then cultured at 37° C. for 7-10 days, during which the adipocyte differentiation medium was refreshed every 3 days. Finally, the medium was removed, and the cells of each group were washed with PBS and subjected to oil red O staining for determination of the fat content. The relative fat content is a ratio of the cellular fat content of the experimental group relative to that of the control group (expressed as a percentage). The adipocytes of the control group were treated similarly with the adipocyte differentiation medium free of a plant extract.

TABLE 1

| Groups | Treatments | Relative fat content |
| --- | --- | --- |
| Control | — | 100% |
| Comparative group 1 | Black tea 0.0625 mg/ml | 94.60% |
| Comparative group 2 | Red wine 0.0625 mg/ml | 102.80% |
| Comparative group 3 | Green tea 0.0625 mg/ml | 92.40% |
| Comparative group 4 | Pu-erh tea 0.0625 mg/ml | 93.90% |
| Comparative group 5 | Four Seasons Spring tea 0.0625 mg/ml | 98.70% |
| Comparative group 6 | *Citrus* 0.0625 mg/ml | 123.70% |
| Comparative group 7 | Spinach 0.0625 mg/ml | 118.60% |
| Comparative group 8 | Green coffee bean 0.0625 mg/ml | 110.00% |
| Comparative group 9 | Blueberry 0.0625 mg/ml | 156.40% |
| Comparative group 10 | Turmeric 0.125 mg/ml | 94.70% |
| Comparative group 11 | Lycopene 0.015625 mg/ml | 73.34% |
| Comparative group 12 | Broccoli sprout 0.125 mg/ml | 76.63% |

TABLE 1-continued

| Groups | Treatments | Relative fat content |
|---|---|---|
| Comparative group 13 | Apple polyphenols 0.015625 mg/ml | 92.00% |
| Comparative group 14 | β-carotene 0.5 mg/ml | 99.00% |
| Comparative group 15 | Ginseng 0.125 mg/ml | 125.78% |
| Comparative group 16 | Wolfberry 1 mg/ml | 127.13% |
| Comparative group 17 | Garlic 1 mg/ml | 114.01% |
| Comparative group 18 | Red clover 0.5 mg/ml | 81.46% |
| Comparative group 19 | Aloe 1 mg/ml | 118.60% |
| Comparative group 20 | Rosemary 0.0625 mg/ml | 84.64% |
| Comparative group 21 | Pepper 0.5 mg/ml | 108.83% |
| Comparative group 22 | Spinach + Lycopene 0.015625 mg/ml + 0.015625 mg/ml | 76.28% |
| Comparative group 23 | Spinach + Broccoli sprout 0.125 mg/ml + 0.125 mg/ml | 82.17% |
| Comparative group 24 | Spinach + Aloe 1 mg/ml + 1 mg/ml | 102.24% |
| Comparative group 25 | Spinach + Pepper 0.5 mg/ml + 0.5 mg/ml | 114.07% |
| Experimental group 1 | Blueberry + Black tea 0.0625 mg/ml + 0.0625 mg/ml | 67.50% |
| Experimental group 2 | Blueberry + Green tea 0.0625 mg/ml + 0.0625 mg/ml | 70.90% |
| Experimental group 3 | Red wine + Black tea 0.0625 mg/ml + 0.0625 mg/ml | 57.90% |
| Experimental group 4 | Red wine + Green tea 0.0625 mg/ml + 0.0625 mg/ml | 60.10% |
| Experimental group 5 | Red wine + Pu-erh tea 0.0625 mg/ml + 0.0625 mg/ml | 60.00% |
| Experimental group 6 | Red wine + Four Seasons Spring tea 0.0625 mg/ml + 0.0625 mg/ml | 56.90% |
| Experimental group 7 | Red wine + *Citrus* 0.0625 mg/ml + 0.0625 mg/ml | 48.20% |
| Experimental group 8 | Red wine + Spinach 0.0625 mg/ml + 0.0625 mg/ml | 59.10% |
| Experimental group 9 | Red wine + Green coffee bean 0.0625 mg/ml + 0.0625 mg/ml | 50.80% |
| Experimental group 10 | Citrus + Turmeric 0.125 mg/ml + 0.125 mg/ml | 89.05% |
| Experimental group 11 | Citrus + Lycopene 0.015625 mg/ml + 0.015625 mg/ml | 70.51% |
| Experimental group 12 | Citrus + Broccoli sprout 0.125 mg/ml + 0.125 mg/ml | 57.80% |
| Experimental group 13 | Citrus + Apple polyphenols 0.015625 mg/ml + 0.015625 mg/ml | 64.16% |
| Experimental group 14 | Citrus + β-carotene 0.5 mg/ml + 0.5 mg/ml | 66.16% |
| Experimental group 15 | Citrus + Ginseng 0.125 mg/ml + 0.125 mg/ml | 70.16% |
| Experimental group 16 | Citrus + Wolfberry 1 mg/ml + 1 mg/ml | 69.45% |
| Experimental group 17 | Citrus + Garlic 1 mg/ml + 1 mg/ml | 92.82% |
| Experimental group 18 | Citrus + Red clover 0.5 mg/ml + 0.5 mg/ml | 86.87% |
| Experimental group 19 | Citrus + Aloe 1 mg/ml + 1 mg/ml | 79.16% |
| Experimental group 20 | Citrus + Rosemary 0.0625 mg/ml + 0.0625 mg/ml | 65.21% |
| Experimental group 21 | Citrus + Pepper 0.5 mg/ml + 0.5 mg/ml | 76.81% |
| Experimental group 22 | Spinach + Turmeric 0.125 mg/ml + 0.125 mg/ml | 75.75% |
| Experimental group 23 | Spinach + Apple polyphenols 0.015625 mg/ml + 0.015625 mg/ml | 88.58% |
| Experimental group 24 | Spinach + β-carotene 0.5 mg/ml + 0.5 mg/ml | 93.82% |
| Experimental group 25 | Spinach + Ginseng 0.125 mg/ml + 0.125 mg/ml | 82.17% |
| Experimental group 26 | Spinach + Wolfberry 1 mg/ml + 1 mg/ml | 80.69% |
| Experimental group 27 | Spinach + Garlic 1 mg/ml + 1 mg/ml | 88.64% |
| Experimental group 28 | Spinach + Red clover 0.5 mg/ml + 0.5 mg/ml | 67.98% |
| Experimental group 29 | Spinach + Rosemary 0.0625 mg/ml + 0.0625 mg/ml | 82.58% |

Figure 2:
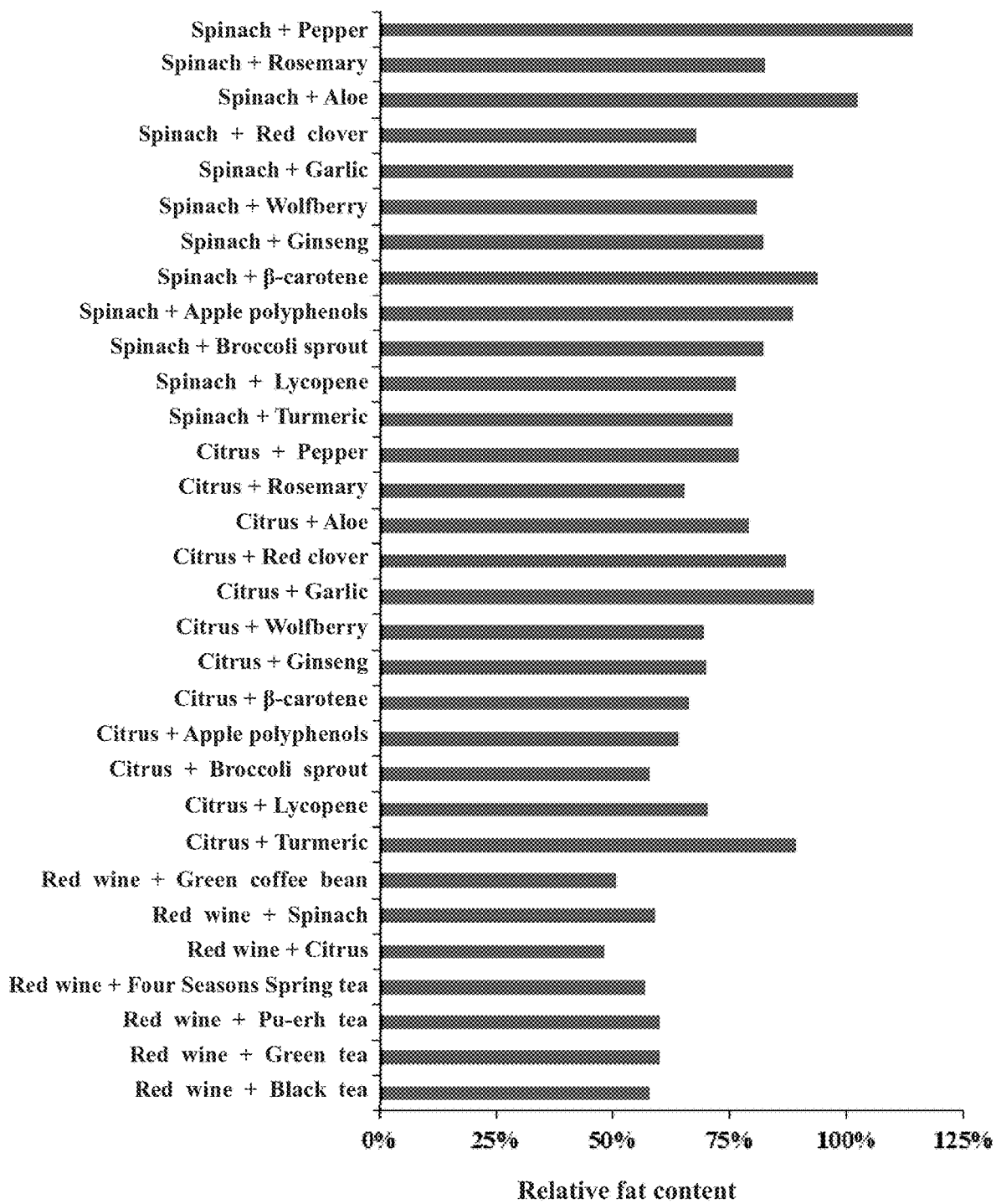
FIG. 2 shows the effect of the various compositions according to one embodiment of the invention on the relative fat content of adipocytes.

TABLE 1 shows the relative fat content of adipocytes after different treatments; FIGS. 1 and 2 are histograms corresponding to the values shown in TABLE 1. According to TABLE 1 and FIG. 1, compared to the control group, the sole treatment with the red wine extract, the Four Seasons Spring tea extract, the citrus extract, the spinach extract, the green coffee bean extract, the blueberry extract, the ginseng extract, the wolfberry extract, the garlic extract, the aloe extract, the pepper extract, or β-carotene did not significantly reduce the fat content of adipocytes. Some of these treatments even significantly increased the fat content, such as treatment with the blueberry extract, the citrus extract, or the spinach extract (see the comparative groups). In addition, the sole treatment with the black tea extract, the green tea extract, the Pu-erh tea extract, the turmeric extract, or apple polyphenols only resulted in a slight decrease in the relative fat content to about 90% or more.

However, the combination of the blueberry extract with the black tea extract or the green tea extract significantly reduced the relative fat content of adipocytes to 67.50% and 70.9%, respectively (see the experimental groups). Also, the combination of the red wine extract with the black tea extract, the green tea extract, the Pu-erh tea extract, the Four Seasons Spring tea extract, the citrus extract, the spinach extract, or the green coffee bean extract significantly reduced the fat content of adipocytes. Moreover, the combination of the citrus extract with the turmeric extract, the broccoli sprout extract, the ginseng extract, the wolfberry extract, the garlic extract, the red clover extract, the rosemary extract, the pepper extract, apple polyphenols, β-carotene, or lycopene also resulted in a significantly lower fat content. Furthermore, the combination of the spinach extract with the turmeric extract, the ginseng extract, the wolfberry extract, the garlic extract, the red clover extract, the rosemary extract, apple polyphenols, or β-carotene significantly reduced the fat content of adipocytes. The compositions having the particular combinations set forth above unexpectedly exhibit higher fat-reducing ability than the sum of the fat-reducing ability for the respective single components.

In conclusion, due to the mix of particular plant extracts or the mix of a particular plant extract and a particular plant-derived compound, the composition of the invention greatly reduces the fat content of fat-producing cells, thereby having the potential to reduce body fat and to prevent obesity associated diseases. Therefore, the composition of the invention, along with a pharmaceutically acceptable carrier, may be used in the manufacture of a pharmaceutical composition for reducing the fat content of fat-producing cells. The pharmaceutical composition may be in the form of a solution, a powder, a capsule, or a tablet, but not limited thereto.

What is claimed is:

1. A method of treating obesity in a human in need thereof comprising administering to the human in need thereof a therapeutically effective amount of a composition comprising at least 0.0625 mg/ml of a red wine extract and at least 0.0625 mg/ml of a Four Seasons spring extract to effectively treat the obesity in said human in need thereof.

2. The method of claim 1, wherein the composition further comprises a pharmaceutically acceptable carrier.

3. The method of claim 2, wherein the composition is in the form of a solution, a powder, a capsule, or a tablet.

* * * * *